United States Patent [19]

Saruyama et al.

[11] Patent Number: 5,470,934
[45] Date of Patent: Nov. 28, 1995

[54] VINYL- AND ALKOXY-FUNCTIONAL ORGANOSILICON COMPOUNDS AND METHOD FOR THE PREPARATION THEREOF

[75] Inventors: Toshio Saruyama; Masahiko Suzuki, both of Chiba, Japan

[73] Assignee: Dow Corning Toray Silicone Co., Ltd., Tokyo, Japan

[21] Appl. No.: 306,788

[22] Filed: Sep. 15, 1994

[30] Foreign Application Priority Data

Sep. 29, 1993 [JP] Japan ................... 5-265585
Nov. 12, 1993 [JP] Japan ................... 5-307367

[51] Int. Cl.$^6$ .................................. C08G 77/18
[52] U.S. Cl. ................. 52.8/34; 528/18; 528/23; 556/453; 556/469; 556/470
[58] Field of Search ................. 556/453, 469, 556/470; 528/34, 23, 18

[56] References Cited

U.S. PATENT DOCUMENTS

| | | | |
|---|---|---|---|
| 5,256,480 | 10/1993 | Inoue et al. | 428/331 |
| 5,300,612 | 4/1994 | Saruyama | 528/17 |
| 5,354,830 | 10/1994 | Williams | 556/469 |

FOREIGN PATENT DOCUMENTS

| | | |
|---|---|---|
| 3197486 | 8/1991 | Japan . |
| 3287664 | 10/1991 | Japan . |
| 3244636 | 10/1991 | Japan . |

OTHER PUBLICATIONS

Chemical Abstracts, vol. 116, No. 22, 1 Jun. 1992, Columbus, Ohio, US; Abstract No. 215662.
Chemical Abstracts, vol. 116, No. 14, 6 Apr. 1992, Columbus, Ohio, US; Abstract No. 129932Y.
Chemical Abstracts, vol. 115, No. 25, 23 Dec. 1991, Columbus, Ohio, US; Abstract No. 280283N.

*Primary Examiner*—Melvyn I. Marquis
*Attorney, Agent, or Firm*—Roger H. Borrousch

[57] ABSTRACT

Vinyl- and alkoxy-functional organosilicon compounds with the general formula $$(CH_2=CH-\underset{\underset{CH_3}{|}}{\overset{\overset{CH_3}{|}}{Si}}-O)_a Si(OR)_{4-(a+b)}(CH=CH_2)_b$$

in which R denotes $C_1$ and $C_4$ alkyl and a is 1, 2, or 3, b is 0 or 1, and a+b is 2 or 3 are made by an exchange reaction between sym-divinyltetramethyldisiloxane and vinyltrialkoxysilane or tetraalkoxysilane. These novel vinyl- and alkoxy-functional organosilicon compounds exhibit a high condensation reactivity with the silanol group.

11 Claims, 8 Drawing Sheets

VINYL- AND ALKOXY-FUNCTIONAL ORGANOSILICON COMPOUNDS AND METHOD FOR THE PREPARATION THEREOF

BACKGROUND OF THE INVENTION

1. Technical Field

The invention relates to novel vinyl- and alkoxy-functional organosilicon compounds and to a method for the preparation thereof. More specifically, the invention relates to novel vinyl- and alkoxy-functional organosilicon compounds that contain alkoxy that is highly reactive with the silanol group and to a method for the preparation thereof.

2. Background Information

A large number of alkoxy-functional organosilicon compounds in which alkoxy is bonded to silicon are already known. These are widely used as coupling agents for bonding glass fibers and organic resins and as chain extenders and crosslinkers for silicone polymers and organic polymers. Known examples of these alkoxy-functional organosilicon compounds include monofunctional alkoxysilanes (1 silicon-bonded alkoxy group is present), difunctional alkoxysilanes (2 silicon-bonded alkoxy groups are present), trifunctional alkoxysilanes (3 silicon-bonded alkoxy groups are present), and tetrafunctional alkoxysilanes (4 silicon-bonded alkoxy groups are present). As the number of alkoxy groups in these alkoxysilanes diminishes, the hydrolyzability of the alkoxy groups and their condensation reactivity with the silanol group both decline. As a consequence, the difunctional alkoxysilanes and trifunctional alkoxysilanes are substantially less reactive than the tetrafunctional alkoxysilanes. This has created demand for alkoxy-functional organosilicon compounds that can exhibit the high reactivity of the tetrafunctional alkoxysilanes. The inventors have already proposed an alkoxy-functional organosilicon compound with the following formula for use as a chain extender in U.S. Pat. No. 5,300,612, issued Apr. 5, 1994, to Toshio Saruyama,

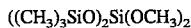

$((CH_3)_3SiO)_2Si(OCH_3)_2$

However, the alkoxy groups in this particular alkoxy-functional organosilicon compound do not have a very high condensation reactivity with the silanol group, and this compound is therefore not fully satisfactory for some applications. On the other hand, the vinyl-containing alkoxysilanes, as typified by vinylmethyldimethoxysilane and vinyltrimethoxysilane, contain a different type of alkoxy-functional group in terms of the alkoxysilyl moiety, and one would expect that they could also be used as chain extenders and crosslinkers. Unfortunately, the alkoxy group in these vinyl-containing alkoxysilanes also exhibits an unsatisfactory condensation reactivity with the silanol group.

SUMMARY OF THE INVENTION

Problems to be Solved by the Invention

The inventors achieved the invention as the result of extensive investigations directed as solving the problems described above.

In specific terms, the invention takes as its object novel vinyl- and alkoxy-functional organosilicon compounds that contain the vinyl group, as well as, the silicon-bonded alkoxy group that has a high condensation reactivity with the silanol group. An additional object of the invention is a method for the preparation of said novel organosilicon compounds. A further object of this invention is novel room temperature vulcanizable silicone compositions prepare with these novel vinyl- and alkoxy-functional organosilicon compounds.

Means Solving the Problems and Function Thereof

The invention relates to vinyl- and alkoxy-functional organosilicon compounds with the general formula

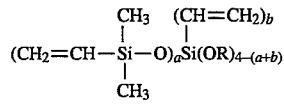

$$(CH_2=CH-\underset{\underset{CH_3}{|}}{\overset{\overset{CH_3}{|}}{Si}}-O)_a Si(OR)_{4-(a+b)} \overset{(CH=CH_2)_b}{}$$

in which R denotes $C_1$ and $C_4$ alkyl and a is 1, 2, or 3, b is 0 or 1, and a+b is 2 or 3.

Another preferred embodiment of this invention is a method for the preparation of a vinyl- and alkoxy-functional organosilicon compound with a general formula

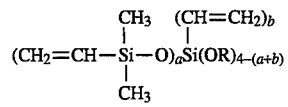

$$(CH_2=CH-\underset{\underset{CH_3}{|}}{\overset{\overset{CH_3}{|}}{Si}}-O)_a Si(OR)_{4-(a+b)} \overset{(CH=CH_2)_b}{}$$

in which R denotes $C_1$ to $C_4$ alkyl and a is 1, 2, or 3, b is 0 or 1, and a+b is 2 or 3, comprising mixing sym-divinyltetramethyldisiloxane and vinyltrialkoxysilane or tetraalkoxysilane in the presence of an acid catalyst and heating at a temperature of from 70° C. and 150° C. promoting an exchange reaction between sym-divinyltetramethyldisiloxane and vinyltrialkoxysilane or heating at a temperature of from 70° C. to 200° C. promoting an exchange reaction between sym-divinyltetramethyldisiloxane and tetraalkoxysilane.

BRIEF DESCRIPTION OF THE FIGURE DRAWINGS

FIG. 1 contains the infrared absorption spectrogram of the (vinyl+alkoxy)-functional organosilicon compound synthesized in Example 1.

FIG. 2 contains the $^1$H-nuclear magnetic resonance spectrogram of the (vinyl+alkoxy)-functional organosilicon compound synthesized in Example 1.

FIG. 3 contains the infrared absorption spectrogram of the (vinyl+alkoxy)-functional organosilicon compound synthesized in Example 2.

FIG. 4 contains the $^1$H-nuclear magnetic resonance spectrogram of the (vinyl+alkoxy)-functional organosilicon compound synthesized in Example 2.

FIG. 5 contains the IR absorption spectrum of the (vinyl+alkoxy)-functional organosilicon compound manufactured in Application Example 3 of this invention.

FIG. 6 contains the $^1$H-NMR spectrum of the (vinyl+alkoxy)-functional organosilicon compound manufactured in Application Example 3 of this invention.

FIG. 7 contains the IR absorption spectrum of the (vinyl+alkoxy)-functional organosilicon compound manufactured in Application Example 4 of this invention.

FIG. 8 contains the 1H-NMR spectrum of the (vinyl+alkoxy)-functional organosilicon compound manufactured in Application Example

DETAILED DESCRIPTION OF PREFERRED EMBODIMENTS

Figure 1:
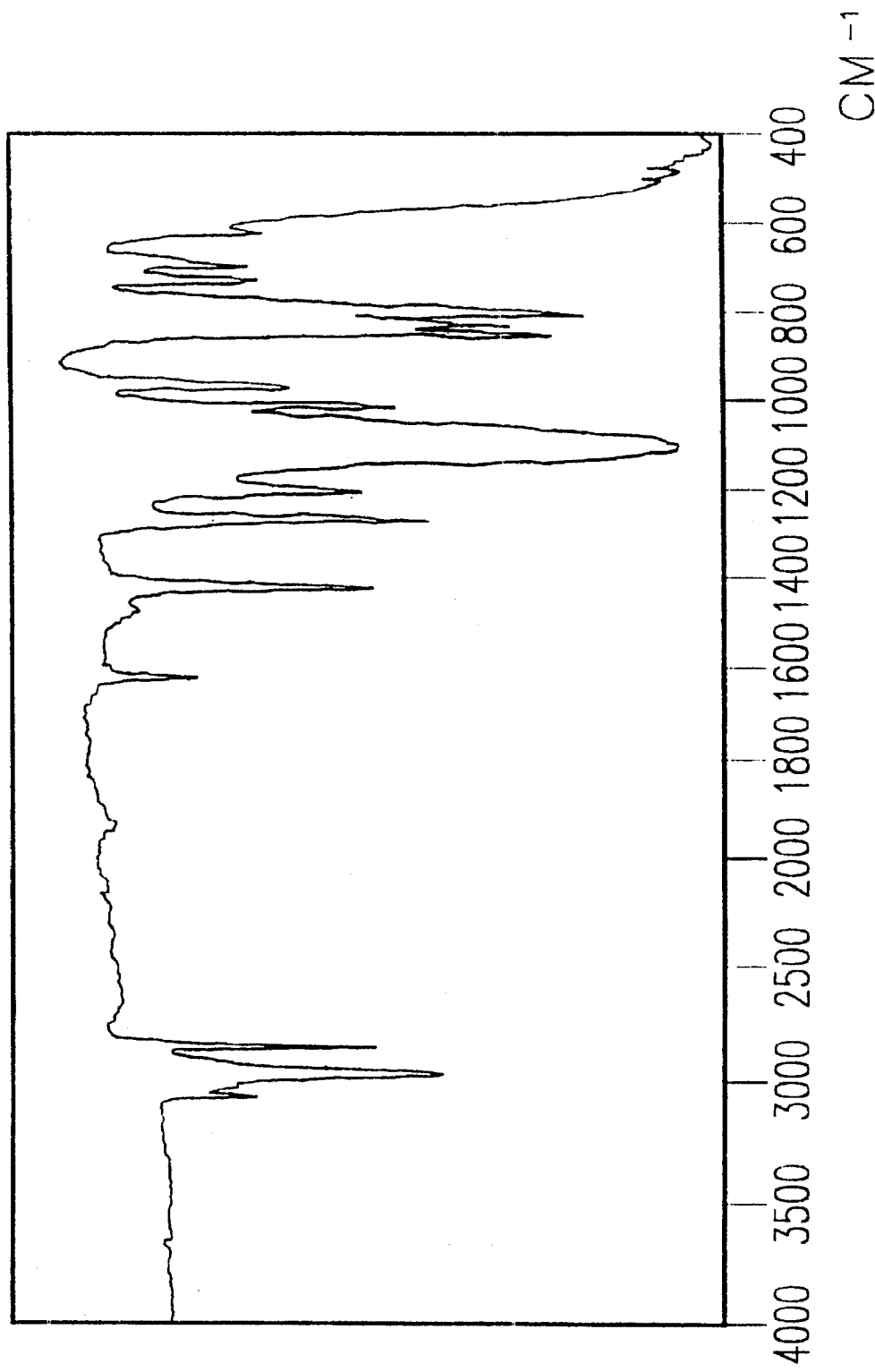

The vinyl- and alkoxy-functional organosilicon compounds according to the present invention are expressed by the following general formula.

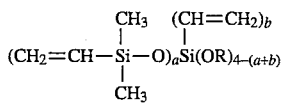

in which R in the preceding formula denotes $C_1$ to $C_4$ alkyl and is exemplified by methyl, ethyl, n-propyl, isopropyl, n-butyl, isobutyl, and tert-butyl. Methyl and ethyl are preferred among the preceding examples, and the methyl group is particularly preferred. The subscript a has a value of 1, 2, or 3. The subscript b is 0 or 1. The sum of a+b is 2 or 3. The subject (vinyl+alkoxy)-functional organosilicon compounds are specifically exemplified by compounds with the following formulas, in which Vi=vinyl, Me=methyl, and Et=ethyl.

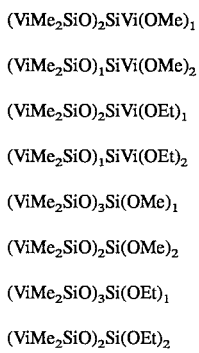

The (vinyl+alkoxy)-functional organosilicon compounds according to the invention can be prepared by running an acid-catalyzed exchange reaction between sym-divinyltetramethyldisiloxane and vinyltrialkoxysilane or an acid-catalyzed exchange reaction between sym-divinyltetramethyldisiloxane and tetraalkoxysilane.

The sym-divinyltetramethyldisiloxane, vinyltrialkoxysilane, and tetraalkoxysilane used in the preparative method of the invention are widely used in industry. Examples of such vinyltrialkoxysilanes are vinyltrimethoxysilane, vinyltriethoxysilane, and vinyltri-n-propoxysilane. Examples of tetraalkoxysilane are tetramethoxysilane, tetraethoxysilane, tetra-(n-propoxy)silane, and tetra-(isobutoxy)silane.

In regard to the quantities of sym-divinyltetramethyldisiloxane and vinyltrialkoxysilane used in the preparative method of the present invention, the standard addition is in general 1 mole or 2 moles sym-divinyltetramethyldisiloxane per 1 mole vinyltrialkoxysilane in order to introduce, respectively, 1 or 2 $ViMe_2SiO$ groups (Vi=vinyl, Me=methyl) into the vinyltrialkoxysilane.

In regard to the quantities of sym-divinyltetramethyldisiloxane and tetraalkoxysilane used in the preparative method of this invention, when 2 or 3 $ViMe_2SiO$ groups (where Vi represents a vinyl group, and Me represents a methyl group) are to be introduced into tetraalkoxysilane, the amount of sym-divinyltetramethyldisiloxane to be used with respect to 1 mole of tetraalkoxysilane should be 2 moles or 3 moles, respectively.

Any acid catalyst may be used in the preparative method of the invention that does not have a negative influence on the reaction system. The acid catalyst is specifically exemplified by acid-treated inorganic compounds such as activated clay, trifulorosulfonic acid, and dodecylbenzene-sulfonic acid.

The reaction product afforded by the sym-divinyltetramethyldisiloxane and vinyltrialkoxysilane exchange reaction comprises a mixture whose components are organosilicon compounds with the formula $(ViMe_2SiO)_xSiVi(OR)_{3-x}$ in which R denotes $C_1$ to $C_4$ alkoxy, x=0 to 3, Vi=vinyl, and Me=methyl. Vinyl- and alkoxy-functional organosilicon compounds of this invention can be obtained by distilling this mixture. One molecule of vinyldimethylalkoxysilane $ViMe_2SiOR$ (R denotes $C_1$ to $C_4$ alkyl, Vi =vinyl, Me=methyl) is produced in this exchange reaction as by-product for each alkoxy group in the vinyltrialkoxysilane that is replaced by the group of the formula $ViMe_3SiO$ (Vi=vinyl, Me =methyl). Accordingly, the reaction is preferably promoted by distilling the former compound. The vinyldimethyl-alkoxysilane by-product can be hydrolyzed to make sym-divinyltetramethyldisiloxane, which can be re-used as starting material in the preparative method of the invention. Other organosilicon compound by-products can be re-used by addition to a subsequent exchange reaction. The subject exchange reaction begins at around 70° C. and ultimately finishes at 100° C. to 150° C. The temperature at which the vinyldimethylalkoxysilane by-product can be distilled rises as the reaction progresses. The acid catalyst is preferably eliminated from the reaction product after completion of the reaction, by neutralization and/or filtration of the reaction product. This reaction may be run in organic solvent.

The product of the exchange reaction between sym-divinyltetramethyldisiloxane and the tetraalkoxysilane is a mixture comprises of the organosilicon compounds represented by the formula $(ViMe_2SiO)_ySi(OR)_{3-y}$ (where, R represents a $C_{1-4}$ alkyl group, y represents a number 0, 1, 2, 3, or 4; Vi represents a vinyl, and Me represents methyl). By distilling said mixture, vinyl- and alkoxy-functional organosilicon compounds of this invention can be obtained. In this exchange reaction, each time one of the alkoxy groups in the tetraalkoxy-silane is substituted by the group represented by the formula $ViMe_2SiO$ (where Vi represents a vinyl group, and Me represents a methyl group), one molecule of vinyldimethylalkoxysilane represented by formula $ViMe_2SiOR$ (where R represents a $C_{1-4}$ alkyl group, Vi represents a vinyl group, and Me represents a methyl group) is generated as a by-product. Consequently, it is preferred that it be removed by distillation while the reaction is carried out. The vinyldimethylalkoxysilane by-product is hydrolyzed to sym-divinyltetramethyldisiloxane, which is recycled as the feed material in the manufacturing method of this invention. Also, other organosilicon compound by-products may be recycled to the exchange reaction. This exchange reaction starts at near 70° C., and it finally reaches completion at 150° to 200° C. As the reaction progresses, the temperature at which the vinyldimethylalkoxysilane by-product can be removed by distillation is increased. After the reaction is completed, it is preferred that the reaction product be neutralized or filtered, to remove the acidic catalyst. Also, it is possible to carry out this reaction in the presence of an organic solvent.

In the vinyl- and alkoxy-functional organosilicon compounds of the present invention, a single silicon atom carried the alkoxy groups, vinyl group in some compounds, and dimethylvinylsiloxy groups. The alkoxy group has a high condensation reactivity with the silanol group as a result, while these compounds can also participate in other reaction by virtue of the presence of the vinyl group. The utilization of these distinguishing features makes the invention compounds extremely useful as coupling agents for bonding glass fibers and organic resins and as chain extenders and crosslinkers for silicone polymers and organic polymers. Compositions which cure at room temperature can be obtained by using the vinyl- and alkoxy-functional organosilicon compounds of this invention in combination with polydiorganosiloxanes with condensable groups, such as hydroxyl endblocked polydimethylsiloxane. A composition of this invention which cures at room temperature comprises a polydiorganosiloxane with silicon bonded hydrolyzable groups and a vinyl- and alkoxy-functional organosilicon compound with a general formula

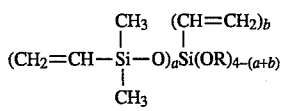

in which R denotes $C_1$ and $C_4$ alkyl and a is 1, 2, or 3, b is 0 or 1, and a+b is 2 or 3. Other ingredients can also be present with the condensable polydiorganosiloxane and vinyl- and alkoxy-functional organosilicon compounds of this invention, such as crosslinkers, fillers, and catalysts. These ingredients are well known in the art of making silicon sealants.

The invention is explained in greater detail through the following working examples. In the examples, Vi indicates the vinyl group and Me indicates the methyl group. The vinyl- and alkoxy-functional organosilicon compounds were determined by $^1$H-nuclear magnetic resonance analysis and infrared spectroscopic analysis. The values reported for the viscosity were measured at 25° C.

EXAMPLE 1

Figure 2:
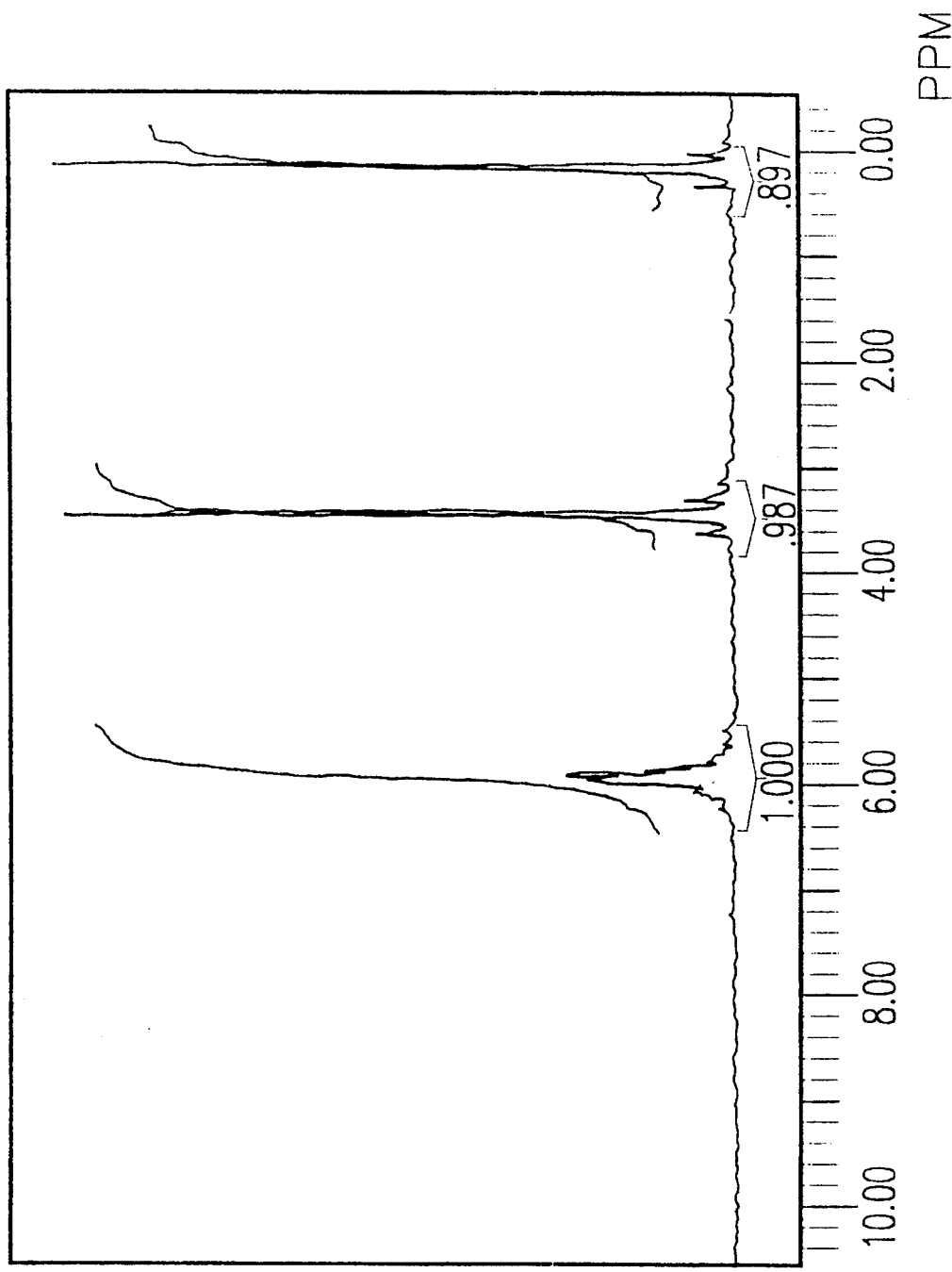

The following were introduced into a 1-liter four-neck flash equipped with a stirrer, thermometer, and simple distillation setup: 296.4 g (2.0 moles) vinyltrimethoxysilane, 372.4 g (2.0 moles) sym-divinyltetramethyldisiloxane, and 6.7 g cation-exchange resin (brand name: Diaion RCP150HD from Mitsubishi Kasei Kabushiki Kaisha, Japan). A reaction was run with stirring and heating until the liquid temperature reached 100° C. Vinyldimethylalkoxysilane by-product was distilled from the reaction system during the course of the reaction. The reaction mixture was sampled at intervals during the reaction and the samples were analyzed by gas chromatographic analysis. The (vinyl+alkoxy)-functional organosilicon compound with the formula $(ViMe_2SiO)SiVi(OMe)_2$ accounted for 35 to 40 weight% of the reaction mixture 20 hours after the start of the reaction. The reaction was stopped at this point, and, after cooling, the reaction mixture was filtered to eliminate the cation-exchange resin. The filtered reaction mixture was then fractionated on a Vigreux distillation setup to give 170 g of a crude fraction with a high content of (vinyl+alkoxy)-functional organosilicon compound with the formula $(ViMe_2SiO)SiVi(OMe)_2$. This crude fraction was subjected to vacuum distillation using a spinning band precision distillation apparatus to give 36 g (vinyl+alkoxy)-functional organosilicon compound with the formula $(ViMe_2SiO)SiVi(OMe)_2$ at bp 71° C./20 mmHg. This (vinyl+alkoxy)-functional organosilicon compound had a purity of 99% and a refractive index of 1.4080. FIG. 1 shows the infrared absorption spectrogram of the (vinyl+alkoxy)-functional organosilicon compound with the formula $(ViMe_2SiO)SiVi(OMe)_2$ produced in this example FIG. 2 the $^1$H-nuclear magnetic resonance spectrogram of the (vinyl+alkoxy)-functional organosilicon compound with the formula $(ViMe_3SiO)SiVi(OMe)_2$ produced in this example.

EXAMPLE 2

Figure 3:
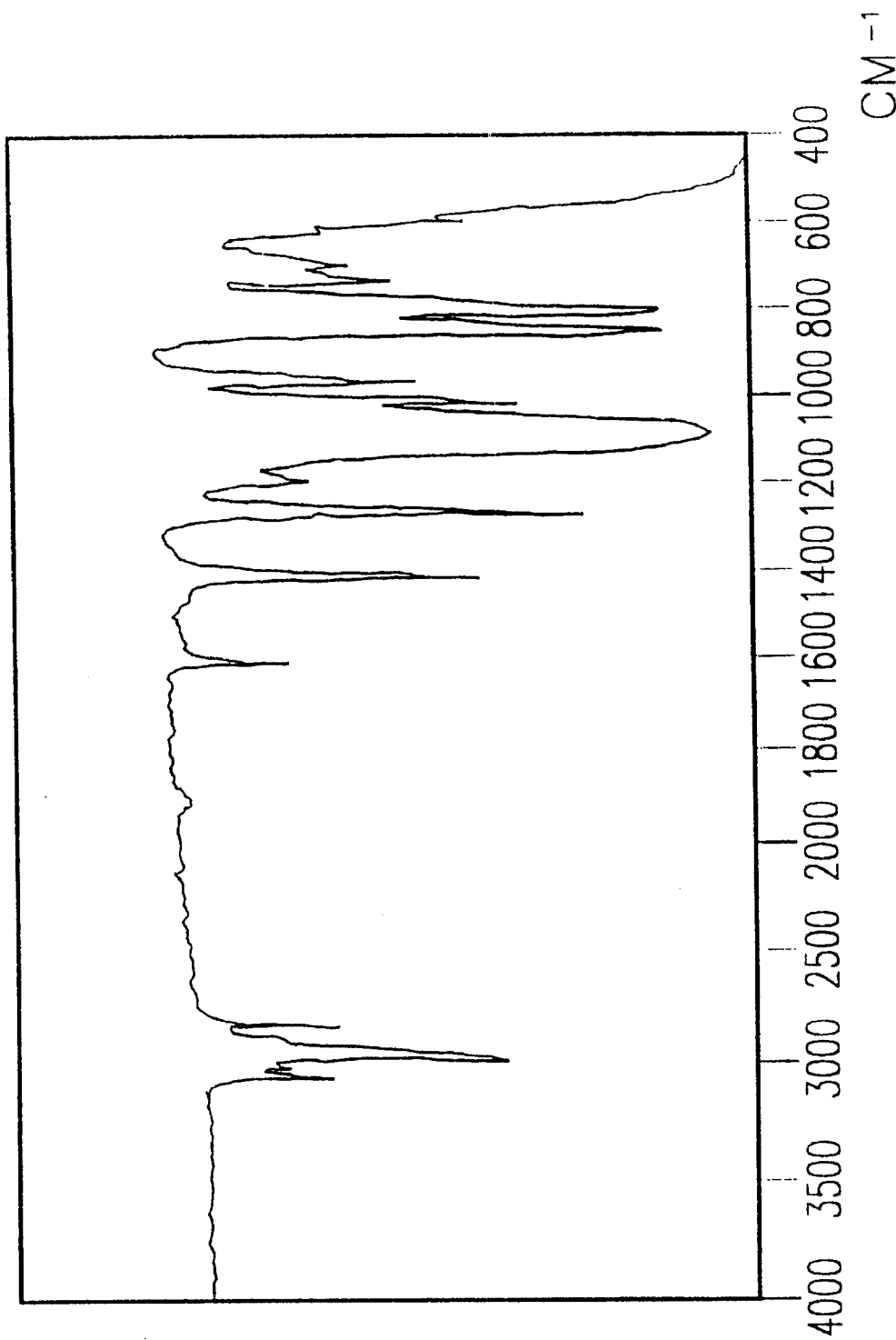
Figure 4:
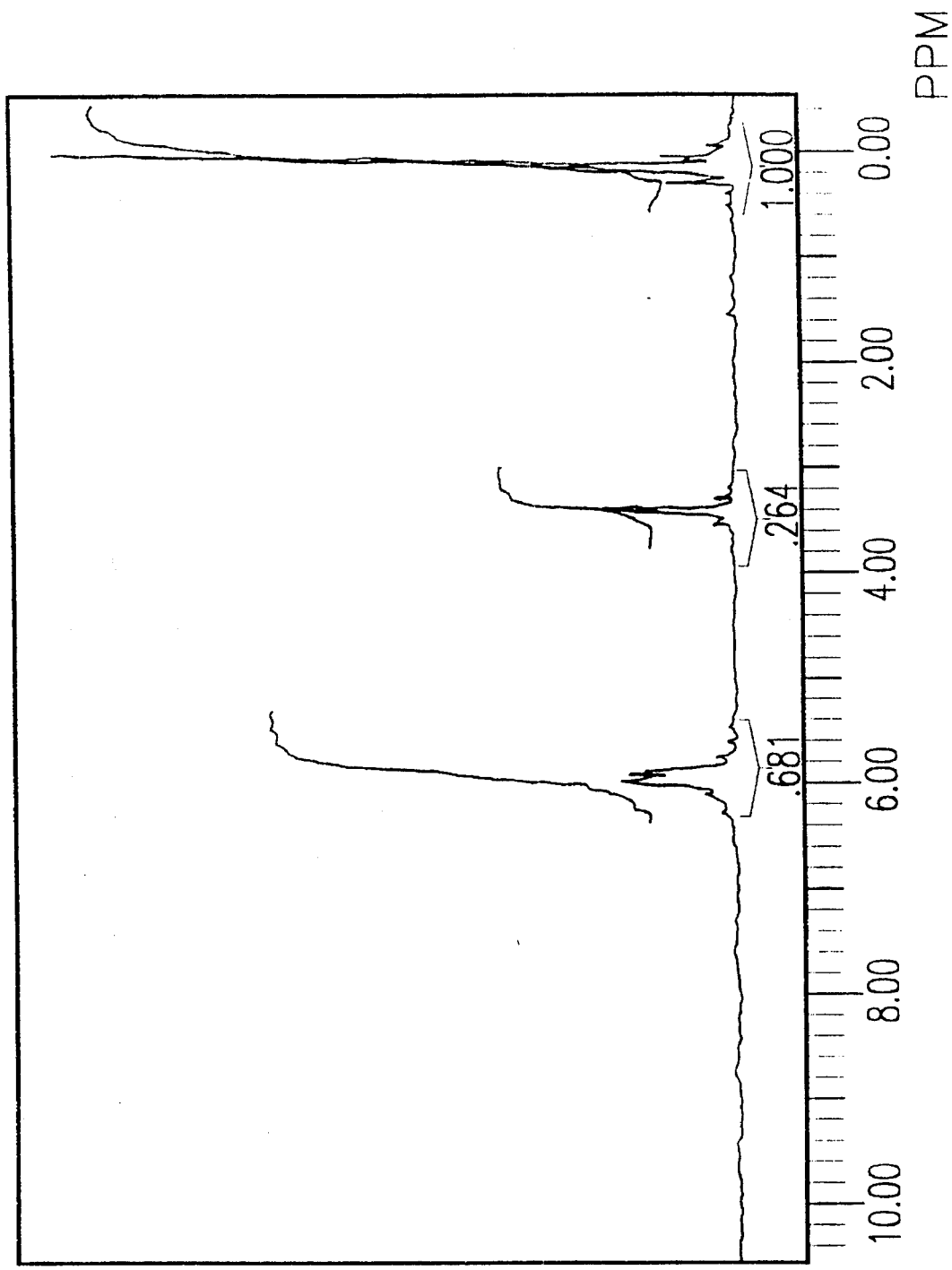

Filtered reaction mixture obtained according to Example 1 was fractionated on a Vigreux distillation setup to give 45 g of a crude fraction with a high content of (vinyl+alkoxy)-functional organosilicon compound with the formula $(ViMe_2SiO)_2SiVi(OMe)$. This crude fraction was subjected to vacuum distillation using a spinning band precision distillation apparatus to give 28 g (vinyl+alkoxy)-functional organosilicon compound with the formula $(ViMe_2SiO)_2SiVi(OMe)$ at bp 102° C./20 mmHg. This (vinyl+alkoxy)-functional organosilicon compound had a purity of 98% and a refractive index of 1.4161. FIG. 3 shows the infrared absorption spectrogram of the (vinyl+alkoxy)-functional organosilicon compound with the formula $(ViMe_2SiO)_2SiVi(OMe)$ produced in this example. FIG. 4 shows the $^1$H-nuclear magnetic resonance spectrogram of the (vinyl+alkoxy)-functional organosilicon compound with the formula $(ViMe_2SiO)_2SiVi(OMe)$ produced in this example.

APPLICATION EXAMPLE 1

In this application example, (vinyl+alkoxy)-functional organosilicon compound according to the invention was evaluated for its reactivity with silanol-endblocked dimethylpolysiloxane.

A mixture of 0.3 g of the (vinyl+alkoxy)-functional organosilicon compound prepared in Example 1 and 0.03 g dibutyltin dilaurate was mixed to homogeneity into 5 g silanol-endblocked dimethylpolysiloxane (viscosity=12.5 Pa.s) to give a room temperature-curing organopolysiloxane composition. This composition was then held at ambient temperature. Its viscosity change, calculated according to the following equation, was determined after 3 hours to be 1280%.

$$\text{Viscosity Change (\%)} = \frac{\text{Viscosity After 3 hours} - \text{Viscosity Immediately After Preparation}}{\text{Viscosity Immediately After Preparation}} \times 100$$

For purposes of comparison, a room temperature-curing organopolysiloxane composition was prepared as above, but in this case using organosilicon compound with the formula $(Me_3SiO)_2Si(OMe)$, (Me=methyl) in place of the (vinyl+alkoxy)-functional organosilicon compound prepared in Example 1 and used above. The viscosity change of this composition, measured after 3 hours as above, was 210%.

Also for the purposes of comparison, a room temperature-curing organopolysiloxane composition was prepared as above, but in this case using methylvinyldimethoxysilane in place of the (vinyl+alkoxy)-functional organosilicon compound prepared in Example 1 and used above. The viscosity change of this composition, measured after 3 hours as above, did not exceed 101%.

The preceding results make it clear that the invention (vinyl+alkoxy)-functional organosilicon compound prepared in Example 1 has a very high condensation reactivity with the silanol group.

EXAMPLE 3

Figure 5:
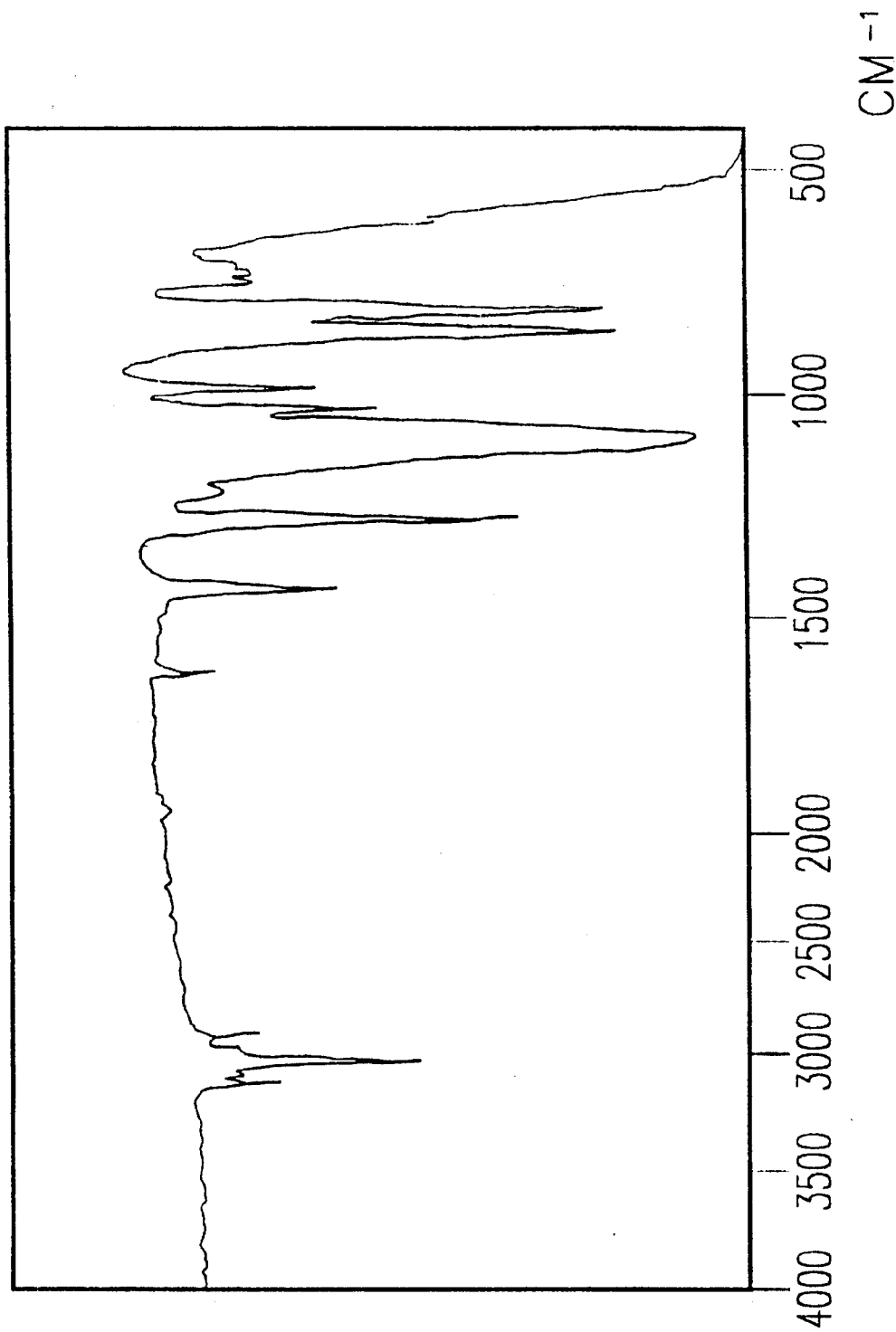
Figure 6:
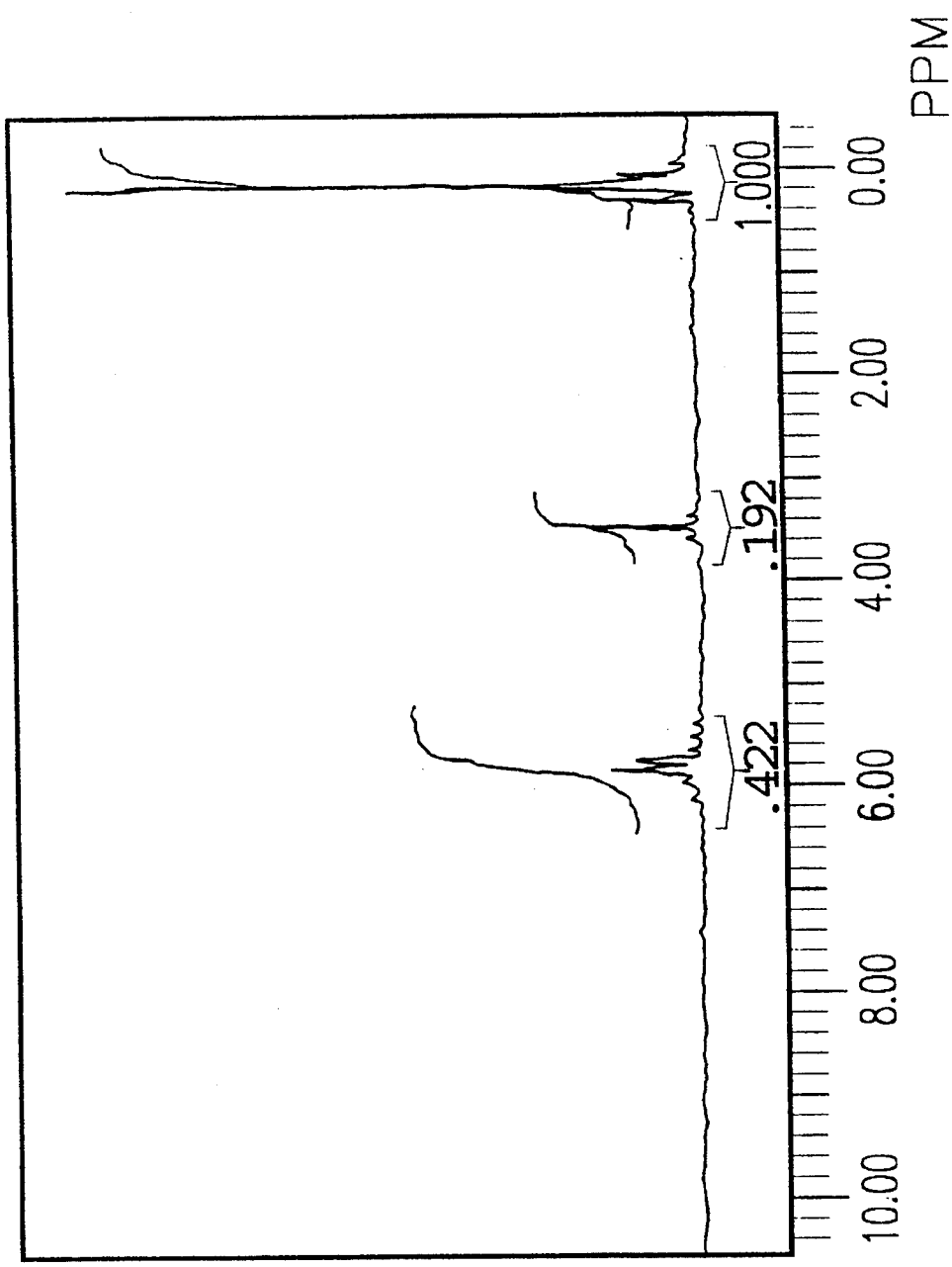

152 g (1.0 mol) of tetramethoxysilane, 558.6 g (3.0mol) of sym-divinyltetramethyldisiloxane, and 7.1 g of a cation-exchange resin (commercial name: Diaion RCP150HD, a product of Mitsubishi Kasei Kabushiki Kaisha, Japan) were loaded into a 1-L four-necked flash equipped with a stirrer, a thermometer and a simple distillation apparatus. The contents were heated to a liquid temperature of 100° C. and the reaction was carried out with stirring. During the reaction process, the vinyldimethylmethoxysilane by-product was removed from the reaction system by distillation. During the heated reaction process, the reaction product was sampled frequently for gas chromatographic analysis. It was found that at the time 36 h after the beginning of the reaction, the content of the (vinyl+alkoxy)-functional organosilicon compound represented by formula $(ViMe_2SiO)_3SiOMe$ was 25–30 wt %. The reaction was stopped at this point. After cooling, the obtained reaction mixture was filtered, and the cation-exchange resin was removed. Then, the filtered reaction mixture was loaded into a Vigreaux fractionating apparatus for fractionation, from which 53.7 g of a crude fraction of distillate containing a large amount of the (vinyl+alkoxy)-functional organisilicon compound represented by the formula $(ViMe_2SiO)_3SiOMe$ were obtained. The crude fraction of distillate was then subjected to distillation under a reduced pressure using a spinning-band precision fractionating apparatus, from which 36 g of the (vinyl+alkoxy)-functional organosilicon compound represented by the formula $(ViMe_2SiO)_3SiOMe$ with a boiling point of 112° C./10 mm Hg were obtained. The purity of the (vinyl+alkoxy)-functional organosilicon compound was 99.9%, and its refractive index was 1.4129. FIG. 5 shows the IR absorption spectrum of the (vinyl+alkoxy)-functional organosilicon compound represented by the formula $(ViMe_2SiO)_3SiOMe$ produced in this example. FIG. 6 shows the $^1$-NMR spectrum of the (vinyl+alkoxy)-functional organosilicon compound represented by the formula $(ViMe_2SiO)_3SiOMe$ produced in this example.

EXAMPLE 4

Figure 7:
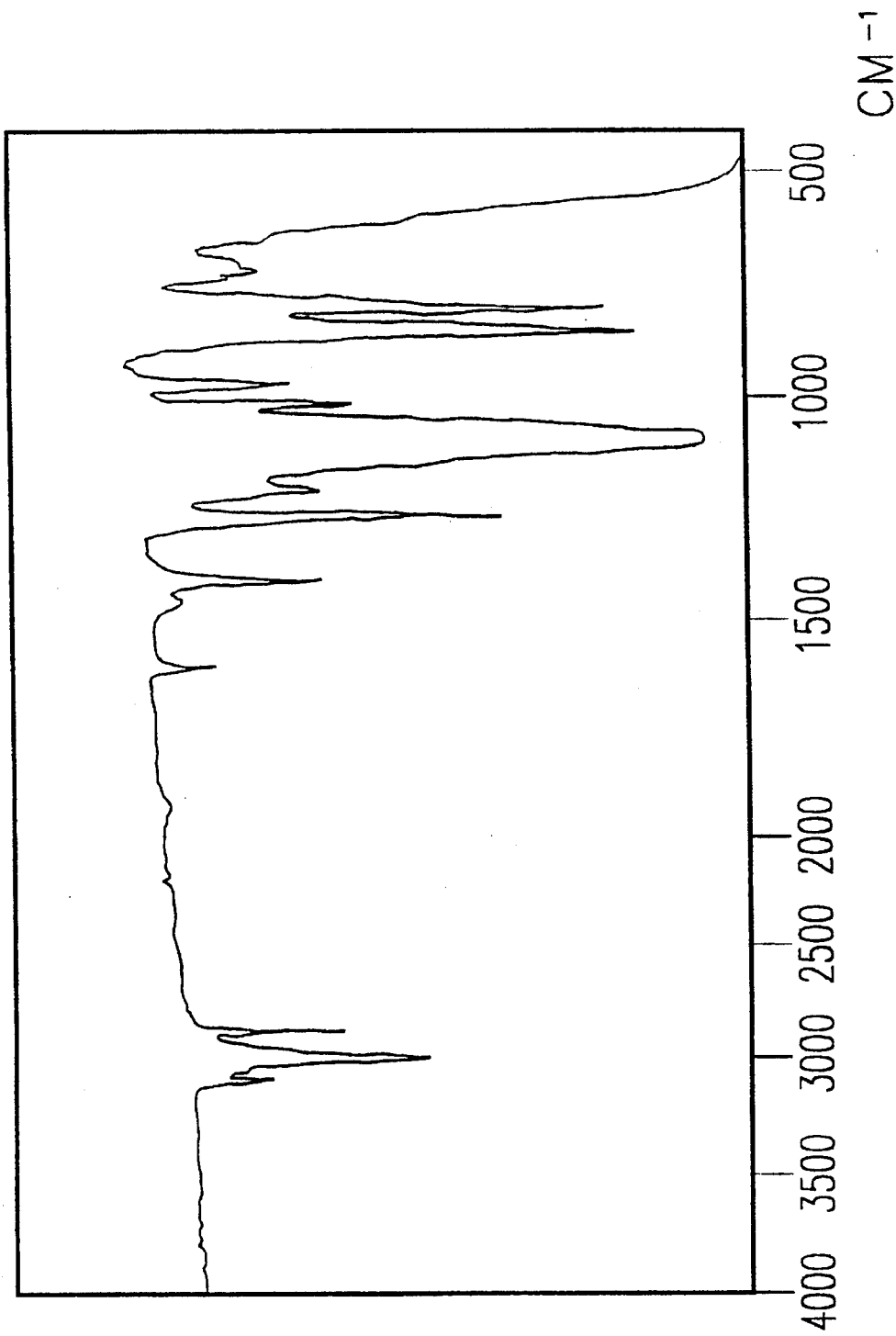
Figure 8:
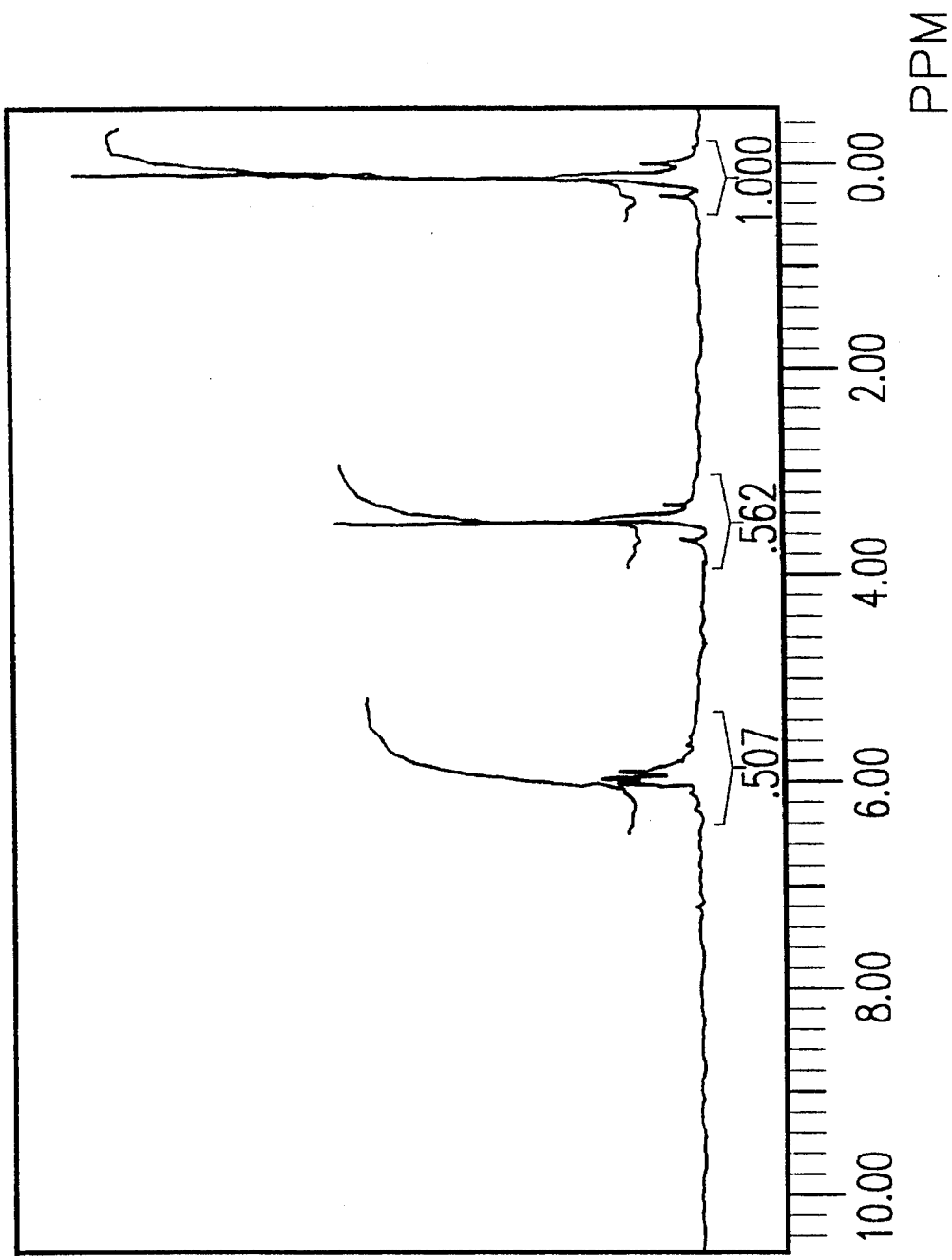

The filtered reaction mixture prepared in the same way as in Example 3 was loaded into a Vigreaux fractionating apparatus for fractionation, from which 112.6 g of a crude fraction of distillate containing a large amount of the (vinyl+alkoxy)functional organosilicon compound represented by the formula $(ViMe_2SiO)_2Si(OMe)_2$ were obtained. The crude fraction of distillate was then subjected to distillation under a reduced pressure using a spinning-band precision fractionating apparatus, from which 60 g of the vinyl+alkoxy)-functional organosilicon compound represented by the formula $(ViMe_2SiO)_2Si(OMe)_2$ with a boiling point of 100° C./20 mm Hg were obtained. The purity of the (vinyl+alkoxy)-functional organosilicon compound was 100%, and its refractive index was 1.4060. FIG. 7 shows the IR absorption spectrum of the (vinyl+alkoxy)-functional organosilicon compound represented by the formula $(ViMe_2SiO_2Si(OMe)_2$ produced in this example. FIG. 8 shows the $^1$H-NMR spectrum of the (vinyl+alkoxy)-functional organosilicon compound represented by the formula $(ViMe_2SiO)_2Si(OMe)_2$ produced in this example.

APPLICATION EXAMPLE 2

The reactivity of the (vinyl+alkoxy)-functional organosilicon compound of this invention with respect to a dimethylpolysiloxane with both terminals blocked by silanols was evaluated. 5 g of dimethylpolysiloxane with both terminals blocked by silanols (viscosity of 12.5 Pa.s) were blended with a mixture of 0.3 g of the (vinyl+alkoxy)-functional organosilicon compound obtained in Example 4 and 0.03 g of dibutyltin laurate uniformly to form an organopolysiloxane that can be cured at room temperature. After the composition was set at room temperature for 3 h, the rate of change in the viscosity was measured and was found to be 320%. The relative viscosity was determined by the formula as described in Application Example 1. In view of the comparisons shown in Application Example 1, it can be concluded that the alkoxyfunctional organosilicon compound obtained in Example 4 of this invention has a very high reactivity with respect to condensation with silanols.

EFFECTS OF THE INVENTION

The (vinyl+alkoxy)-functional organosilicon compounds according to the present invention are novel compounds that contain both the vinyl group and alkoxy that has a high condensation reactivity with the silanol group. The preparative method according to the invention is characterized by the capacity to produce the subject (vinyl+alkoxy)-functional organosilicon compounds in a highly efficient manner.

That which is claimed is:

1. A vinyl- and alkoxy-functional organosilicon compound with a general formula

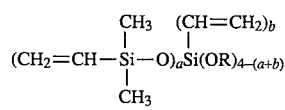

in which R denotes $C_1$ to $C_y$ alkyl and a is 1, 2, or 3, b is 0 or 1, and a+b is 2 or 3.

2. The vinyl- and alkoxy-functional organosilicon compound according to claim 1 in which R is methyl.

3. The vinyl- and alkoxy-functional organosilicon compound according to claim 2 in which a is 3 and b is 0.

4. The vinyl- and alkoxy-functional organosilicon compound according to claim 2 in which a is 2 and b is 1.

5. The vinyl- and alkoxy-functional organosilicon compound according to claim 2 in which a is 2 and b is 0.

6. The vinyl- and alkoxy-functional organosilicon compound according to claim 2 in which a is 1 and b is 1.

7. A method for the preparation of a vinyl- and alkoxy-functional organosilicon compound with a general formula

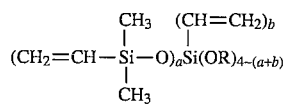

in which R denotes $C_1$ to $C_4$ alkyl and a is 1, 2, or 3, b is 0 or 1, and a+b is 2 or 3, comprising mixing sym-divinyltetramethyldisiloxane and vinyltrialkoxysilane or tetraalkoxysilane in the presence of an acid catalyst and heating at a temperature of from 70° C. and 150° C. promoting an exchange reaction between sym-divinyltetramethyldisiloxane and vinyltrialkoxysilane or heating at a temperature of from 70° C. to 200° C. promoting an exchange reaction between sym-divinyltetramethyldisiloxane and tetraalkoxysilane, where the alkoxy of the vinyltrialkoxysilane and tetraalkoxysilane is oxygen bonded to an alkyl containing from one to four carbons.

8. The method in accordance with claim 7 in which the exchange reaction is between sym-divinyltetramethyldisiloxane and vinyltrialkoxysilane.

9. The method in accordance with claim 7 in which the exchange reaction is between sym-divinyltetramethyldisiloxane and tetraalkoxysilane.

10. A composition curable at room temperature comprising a polydiorganosiloxane with silicon bonded condensable groups and a vinyl- and alkoxy-functional organosilicon compound with a general formula

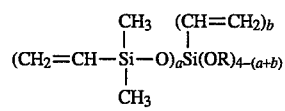

in which R denotes $C_1$ to $C_4$ alkyl and a is 1, 2, or 3, b is 0 or 1, and a+b is 2 or 3.

11. The composition according to claim 10 in which the condensable groups of the polydiorganosiloxane are hydrolyzable groups.